US011530242B2

(12) United States Patent
Chackerian et al.

(10) Patent No.: US 11,530,242 B2
(45) Date of Patent: Dec. 20, 2022

(54) EGFRVIII IMMUNOGEN AND METHODS FOR USING SAME

(71) Applicants: UNM RAINFOREST INNOVATIONS, Albuquerque, NM (US); Bryce Chackerian, Albuquerque, NM (US); Oliver Rixe, Albuquerque, NM (US)

(72) Inventors: Bryce Chackerian, Albuquerque, NM (US); Oliver Rixe, Albuquerque, NM (US)

(*) Notice: Subject to any disclaimer, the term of this patent is extended or adjusted under 35 U.S.C. 154(b) by 0 days.

(21) Appl. No.: 17/259,400

(22) PCT Filed: Jul. 16, 2019

(86) PCT No.: PCT/US2019/042012
§ 371 (c)(1),
(2) Date: Jan. 11, 2021

(87) PCT Pub. No.: WO2020/018540
PCT Pub. Date: Jan. 23, 2020

(65) Prior Publication Data
US 2021/0253641 A1   Aug. 19, 2021

Related U.S. Application Data

(60) Provisional application No. 62/699,072, filed on Jul. 17, 2018.

(51) Int. Cl.
| | |
|---|---|
| *A61K 39/00* | (2006.01) |
| *A61K 39/12* | (2006.01) |
| *C12N 7/00* | (2006.01) |
| *C12N 15/62* | (2006.01) |
| *A61K 38/00* | (2006.01) |
| *C07K 7/08* | (2006.01) |
| *A61K 45/06* | (2006.01) |

(52) U.S. Cl.
CPC ........ *C07K 7/08* (2013.01); *A61K 39/001104* (2018.08); *A61K 45/06* (2013.01); *C12N 7/00* (2013.01); *A61K 2039/6075* (2013.01); *C12N 2795/18123* (2013.01)

(58) Field of Classification Search
CPC .... A61K 39/12; A61K 38/00; A61K 2039/53; C07K 14/005; Y02A 50/30
See application file for complete search history.

(56) References Cited

FOREIGN PATENT DOCUMENTS

| WO | 2004/004661 | 1/2004 |
| WO | 2007/127204 | 11/2007 |
| WO | 2013/103614 | 7/2013 |
| WO | WO2013103614 | * 7/2013 |

OTHER PUBLICATIONS

Jegerlehner et al., "A molecular assembly system that renders antigens of choice highly repetitive for induction of protective B cell responses" 2002 Vaccine, 20:3104-3112.
Quan et al., "Kinetics of immune responses to influenza virus-like particles and dose-dependence of protection with a single vaccination" May 2009 Journal of Virology, 83(9):4489-4497.
PCT/US2019/042012 filed Jul. 16, 2019; International Search Report and Written Opinion dated Nov. 14, 2019; 6 pages.
Ong et al., "Virus like particles as a platform for cancer vaccine development" 2017 PeerJ, 5:e4053.
Choi et al., "EGFRvIII-targeted vaccination therapy of malignant glioma" Oct. 2009 Brain Pathology, 19(4):713-723.
An et al., "Epidermal growth factor receptor (EGFR) and EGFRvIII in glioblastoma (GBM): signaling pathways and targeted therapies" Mar. 2018 Oncogene, 37(12):1561-1575.
PCT/US2019/042012 filed Jul. 16, 2019; International Preliminary Report on Patentability dated Jan. 28, 2021; 5 pages.
Tatusova et al., "Blast 2 Sequences, a new tool for comparing protein and nucleotide sequences" May 1999 FEMS Microbiology Letters 174(2): 247-250.
Chackerian, "Virus-like particles: flexible platforms for vaccine development" 2007 Expert Review of Vaccines, 6(3) 381-390.
Chackerian et al., "Moving towards a new class of vaccines for non-infectious chronic diseases" 2016 Expert Review of Vaccines, 15(5): 561-563.
Clocksin et al., "Virus-like Particle Display Enhances the Immunogenicity of a Candidate Vaccine for Glioblastoma" Western Medical Research Conference. Abstract No. 444, Carmel, California, Jan. 24-26, 2019. Available online [retrieved Jun. 13, 2022] at https://jim.bmj.com/content/67/1/224; 1 page.

* cited by examiner

*Primary Examiner* — Barry A Chestnut
(74) *Attorney, Agent, or Firm* — Mueting Raasch Group

(57) ABSTRACT

An immunogen includes an antigenic EGFRvIII peptide linked to a Qβ bacteriophage virus-like particle (VLP) carrier. The antigenic EGFRvIII peptide has at least 53%, at least 61%, at least 69%, at least 76%, at least 84%, or at least 92% sequence similarity amino acid similarity to LEEKKGNYVVTDH (SEQ ID NO:1).

9 Claims, 1 Drawing Sheet
Specification includes a Sequence Listing.

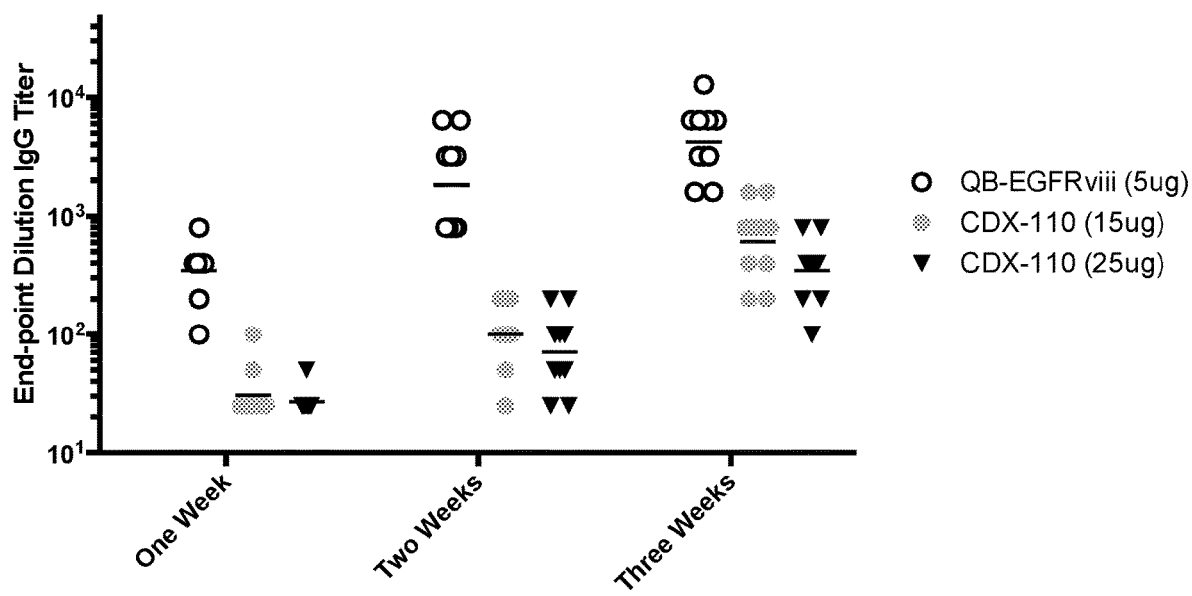

EGFRVIII IMMUNOGEN AND METHODS FOR USING SAME

This application is the § 371 U.S. National Stage of International Application No. PCT/US2019/042012, filed Jul. 16, 2019, which claims the benefit of U.S. Provisional Patent Application No. 62/699,072, filed Jul. 17, 2018, each of which is incorporated herein by reference in its entirety.

SEQUENCE LISTING

This application contains a Sequence Listing electronically submitted via EFS-Web to the United States Patent and Trademark Office as an ASCII text file entitled "0310-000133US01_ST25.txt" having a size of 1 kilobyte and created on Dec. 16, 2020. The information contained in the Sequence Listing is incorporated by reference herein.

SUMMARY

This disclosure describes, in one aspect, an immunogen that includes an antigenic EGFRvIII peptide linked to a Qß bacteriophage virus-like particle (VLP) carrier. The antigenic EGFRvIII peptide has at least 53%, at least 61%, at least 69%, at least 76%, at least 84%, or at least 92% sequence similarity amino acid similarity to LEEKKGNYVVTDH (SEQ ID NO:1).

In some embodiments, the immunogenic carrier is linked to the EGFRvIII peptide through a succinimidyl-6[β-maleimidopropionamido]hexanoate (SMPH) cross-linker molecule.

In another aspect, this disclosure describes a pharmaceutical composition that includes the immunogen summarized above.

In another aspect, this disclosure describes an immunogenic composition that includes the immunogen described above and an adjuvant.

In another aspect, this disclosure describes a method for treating an individual having, or at risk for having, certain forms of cancer characterized, at least in part, by tumor cells that express EGFRvIII. Generally, the method includes administering to the individual a therapeutically effective amount of an immunogen that includes an antigenic EGFRvIII peptide linked to a Qß bacteriophage virus-like particle (VLP) carrier. The antigenic EGFRvIII peptide has at least 53%, at least 61%, at least 69%, at least 76%, at least 84%, or at least 92% sequence similarity amino acid similarity to LEEKKGNYVVTDH (SEQ ID NO:1).

In some embodiments, the method further includes administering to the individual at least one additional therapeutic agent for treating the cancer.

In another aspect, this disclosure describes a nucleic acid encoding any embodiment of the immunogen summarized above.

In another aspect, this disclosure describes an expression vector that includes the nucleic acid that encodes the immunogen.

In another aspect, this disclosure describes a host cell that includes the expression vector that contains the nucleic acid that encodes the immunogen.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. End-point dilution IgG peptide-specific antibody titers in mice immunized with Qß-VLPs (open circles), 5 µg Qß-EGFRvIII (blue circles), 15 µg CDX-110 (red circles), and 25 µg CDX-110 (pink circles). Each data point refers to an individual mouse. Lines denote the geometric mean titer (GMT) of each group.

DETAILED DESCRIPTION OF ILLUSTRATIVE EMBODIMENTS

The epidermal growth factor receptor (EGFR) is a transmembrane cell surface protein that serves as a receptor for specific ligands, including epidermal growth factor (EGF) and transforming growth factor alpha (TGF-alpha). Upon ligand binding, EGFR dimerizes and stimulates intracellular protein-tyrosine cascades, including the MAPK, Akt, and JNK pathways, leading to DNA synthesis and cell proliferation.

Genetic alterations of EGFR are often associated with cancer. For example, a deletion referred to as the EGFRvIII deletion produces a variant form of EGFR gene that lacks the coding sequence corresponding to exons 2 through 7. The EGFRvIII deletion creates a novel fusion junction between two regions of the protein that are normally distant from one another. EGFRvIII is frequently found in human tumors, including 20-35% of glioblastoma multiforme, but also non-small cell lung carcinomas and breast cancers, but it is not expressed in healthy tissue. EGFRvIII has been associated with poor long-term survival in glioblastoma patients.

The EGFRvIII mutation creates a novel peptide epitope that is not found in wild-type EGFR. EGFRvIII is characterized by the amino acid sequence LEEKKGNYVVTDH (SEQ ID NO:1), where LEEKK (amino acids 1-5 of SEQ ID NO:1) is derived from exon 1 of the EGFR gene, G is the result of the exon 1 to 8 fusion, and NYVVTDH (amino acids 7-13 of SEQ ID NO:1) is derived from exon 8.

This 13-amino-acid epitope has been incorporated into a vaccine (CDX-110 or rindopepimut; Celldex Therapeutics, Inc., Hampton, N.J.). The vaccine consists of the 13-amino-acid peptide sequence modified with a C-terminal cysteine and chemically conjugated to keyhole limpet hemocyanin (KLH). In clinical trials, CDX-110 elicited peptide-specific antibody responses and was well tolerated. In Phase II clinical trials, CDX-110-vaccinated patients had a median overall survival of 24.6 months, which is substantially longer than the median survival of a contemporary EGFRvIII glioblastoma cohort (15-16 months). However, larger phase III clinical trials showed little difference in median survival between vaccinated individuals and controls (median survival: 20 months).

A Virus-Like Particle Based Vaccine Targeting EGFRvIII

This disclosure describes an engineered VLP-based vaccine that targets the EGFRvIII splice variant. An EGFRvIII peptide was displayed on bacteriophage VLPs by chemically conjugating a synthetic 14-amino-acid peptide (LEEKKGNYVVTDHC, SEQ ID NO:2; "the LEEK peptide") to Qß bacteriophage VLPs using previously described methods (Jegerlehner et al., 2002, *Vaccine* 20(25-26):3104-3112). The LEEK peptide represents the amino terminus of the EGFRvIII protein with a C-terminal cysteine residue.

The LEEK peptide was synthesized and then conjugated to Qß VLPs using a bifunctional crosslinker with amine-reactive and sulfhydryl-reactive arms (SMPH).

To assess the immunogenicity of Qß-EGFRvIII VLPs and to compare immunogenicity to CDX-110, Balb/c mice were given a single intramuscular injection of vaccine. FIG. 1 shows the end-point dilution IgG antibody titers using sera obtained at one, two, and three weeks. Mice immunized with Qß-EGFRvIII had higher titer antibody responses against the LEEK peptide than mice immunized with CDX-110 at all timepoints. At one week, the mice immunized with Qß-EGFRvIII had a geometric mean titer [GMT] of approximately 350, whereas the two CDX-110 groups had titers that were lower by at least 10-fold. At two weeks, mice immunized with Qß-EGFRvIII had antibody titers that were approximately 20-fold higher than mice immunized with CDX-110. At three weeks, mice immunized with Qß-EGFRvIII had a GMT=4,222, versus 606 and 348 in the two CDX-110 groups. Thus, Qß-EGFRvIII immunization led to more rapid and higher titer antibody responses against the LEEK peptide. Specifically, Qß-EGFRvIII immunization led to a detectable antibody response in as little as one week. In contrast, neither dose of CDX-110 elicited measurable antibody responses at seven days post primary vaccination, which is consistent with previous reports of very low influenza-specific IgG responses in mice seven days after being immunized with influenza-VLPs (Quan et al., 2009, *J Virol* 83(9):4489-4497).

Thus, this disclosure describes a Qβ-VLP-based immunogen that specifically targets EGFRvIII. The immunogen includes the amino acid sequence of SEQ ID NO:1 or a structurally similar peptide. As used herein, a peptide is "structurally similar" to a reference polypeptide if the amino acid sequence of the peptide possesses a specified amount of identity compared to the reference peptide.

Structural similarity of two peptides can be determined by aligning the residues of the two peptides (for example, a candidate polypeptide and the peptide of, for example, SEQ ID NO:1) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate peptide is the peptide being compared to the reference peptide (e.g., SEQ ID NO:1). A candidate peptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, peptides may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

An antigenic EGFRvIII peptide can include amino acids in addition to the amino acid residues of SEQ ID NO:1, so long as the additional amino acids (a) do not eliminate immunogenicity toward EGFRvIII or (b) contain sufficient additional amino acid residues of EGFR so that it elicits antibodies that bind to wild-type EGFR.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also includes the presence of conservative substitutions. A conservative substitution for an amino acid in an immunogenic peptide as described herein may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$. Likewise, biologically active analogs of a polypeptide containing deletions or additions of one or more contiguous or noncontiguous amino acids that do not eliminate a functional activity of the peptide are also contemplated.

In some embodiments, an EGFRvIII-targeting peptide as described herein can include a peptide with at least 53%, at least 61%, at least 69%, at least 76%, at least 84%, or at least 92% sequence similarity to SEQ ID NO:1. That is, an EGFRvIII-targeting polypeptide can include a total of no more than six, no more than five, no more than four, no more than three, no more than two, or no more than one amino acid deletions and non-conservative amino acid substitutions compared to the amino acid sequence of SEQ ID NO:1.

In some embodiments, an EGFRvIII-targeting peptide as described herein can include a peptide with at least 53%, at least 61%, at least 69%, at least 76%, at least 84%, or at least 92% sequence identity to SEQ ID NO:1. That is, an EGFRvIII-targeting polypeptide can include a total of no more than six, no more than five, no more than four, no more than three, no more than two, or no more than one amino acid deletions and amino acid substitutions compared to the amino acid sequence of SEQ ID NO:1.

In some embodiments, an EGFRvIII-targeting peptide as described herein can be designed to provide additional sequences, such as, for example, the addition of added C-terminal or N-terminal amino acids that can, for example, facilitate purification by trapping on columns or use of antibodies. Such tags include, for example, histidine-rich tags that allow purification of polypeptides on nickel columns. Such gene modification techniques and suitable additional sequences are well known in the molecular biology arts. For example, the peptide having the amino acid of SEQ ID NO:2 represents the polypeptide of SEQ ID NOl:1 with a C-terminal cysteine residue to facilitate crosslinking to the Qβ VLP carrier.

The EGFRvIII-targeting Qβ VLP may be used to treat a subject having, or at risk of having, a condition characterized, at least in part, by cells that express EGFRvIII. Such conditions include, but are not limited to, glioblastoma multiforme, ovarian carcinoma, breast carcinoma, non-small cell and other lung carcinomas, prostate cancer, head and neck squamous cell carcinoma, colorectal cancer, bladder cancer, and thyroid cancer.

As used herein, "treat" or variations thereof refer to reducing, limiting progression, ameliorating, or resolving, to any extent, the symptoms or signs related to a condition. A "sign" or "clinical sign" refers to an objective physical finding relating to a particular condition capable of being found by one other than the patient. A "symptom" refers to any subjective evidence of disease or of a patient's condition.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject.

Treatment that is prophylactic—e.g., initiated before a subject manifests a symptom or clinical sign of the condition such as, for example, while a tumor remains subclinical—is referred to herein as treatment of a subject that is "at risk" of having the condition. As used herein, the term "at risk" refers to a subject that may or may not actually possess the described risk. Thus, for example, a subject "at risk" of developing a condition is a subject possessing one or more risk factors associated with the condition such as, for example, genetic predisposition, ancestry, age, sex, geographical location, lifestyle, or medical history.

Accordingly, a composition can be administered before, during, or after the subject first exhibits a symptom or clinical sign of the condition. Treatment initiated before the subject first exhibits a symptom or clinical sign associated with the condition may result in decreasing the likelihood that the subject experiences clinical evidence of the condition compared to a subject to which the composition is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

Thus, the method includes administering an effective amount of the composition to a subject having, or at risk of having, a condition characterized, at least in part, by cells that express EGFRvIII. In this aspect, an "effective amount" is an amount effective to reduce, limit progression, ameliorate, or resolve, to any extent, a symptom or clinical sign related to the condition.

Thus, the EGFRvIII-targeting Qβ VLP described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the EGFRvIII-targeting Qβ VLP without causing any undesirable biological effects or interacting in a deleterious manner with any of the other components of the pharmaceutical composition in which it is contained.

The EGFRvIII-targeting Qβ VLP may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an EGFRvIII-targeting Qβ VLP may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the EGFRvIII-targeting Qβ VLP into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of EGFRvIII-targeting Qβ VLP administered can vary depending on various factors including, but not limited to, the cancer being treated, the weight, physical condition, and/or age of the subject, and/or the route of administration. Thus, the absolute weight of EGFRvIII-targeting Qβ VLP included in a given unit dosage form can vary widely, and depends upon factors such as the species, age, weight and physical condition of the subject, and/or the method of administration. Accordingly, it is not practical to set forth generally the amount that constitutes an amount of EGFRvIII-targeting Qβ VLP effective for all possible applications. Those of ordinary skill in the art, however, can readily determine the appropriate amount with due consideration of such factors.

In some embodiments, the method can include administering sufficient EGFRvIII-targeting Qβ VLP to provide a dose of, for example, from about 50 ng/kg to about 1 mg/kg to the subject, although in some embodiments the methods may be performed by administering EGFRvIII-targeting Qβ VLP in a dose outside this range.

In some embodiments, the method includes administering sufficient EGFRvIII-targeting Qβ VLP to provide a minimum dose of at least 50 ng/kg such as, for example, at least 100 ng/kg, at least 200 ng/kg, at least 300 ng/kg, at least 400 ng/kg, at least 500 ng/kg, at least 600 ng/kg, at least 700 ng/kg, at least 800 ng/kg, at least 900 ng/kg, at least 1 µg/kg, at least 2 µg/kg, at least 5 µg/kg, at least 10 µg/kg, at least 20 µg/kg, at least 50 µg/kg, at least 100 µg/kg, at least 200 µg/kg, or at least 500 µg/kg.

In some embodiments, the method includes administering sufficient EGFRvIII-targeting Qβ VLP to provide a maximum dose of no more than 1 mg/kg, no more than 500 µg/kg, no more than 250 µg/kg, no more than 200 µg/kg, no more than 150 µg/kg, no more than 100 µg/kg, no more than 50 µg/kg, no more than 25 µg/kg, no more than 10 µg/kg, no more than 5 µg/kg, no more than 2 µg/kg, no more than 1 µg/kg, no more than 800 ng/kg, no more than 600 ng/kg, no more than 500 ng/kg, no more than 400 ng/kg, no more than 300 ng/kg, no more than 250 ng/kg, no more than 150 ng/kg, no more than 100 ng/kg, no more than 50 ng/kg, or no more than 25 ng/kg.

In some embodiments, the method includes administering sufficient EGFRvIII-targeting Qβ VLP to provide that falls within a range having as endpoints any minimum dose listed above and any maximum dose listed above that is greater than the minimum does. For example, in some embodiments, the method can includes administering sufficient EGFRvIII-targeting Qβ VLP to provide a dose of from 200 ng/kg to about 10 µg/kg to the subject, for example, a dose of from about 700 ng/kg to about 5 µg/kg.

In some embodiments, EGFRvIII-targeting Qβ VLP may be administered, for example, from a single dose to multiple doses per week, although in some embodiments the method can be performed by administering EGFRvIII-targeting Qβ VLP at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different.

In certain embodiments, EGFRvIII-targeting Qβ VLP may be administered at minimum frequency of at least once per year such as, for example, at least once every six months, at least once every four months, at least once every three months, at least once every two months, at least once per month, or at least once every two weeks.

In certain embodiments, EGFRvIII-targeting Qβ VLP may be administered at maximum frequency of no more than once per week such as, for example, no more than once every two weeks, no more than once per month, no more than once every two months, no more than once every three months, no more than once every six months, or once per year.

In some embodiments, EGFRvIII-targeting Qβ VLP may be administered at a frequency defined by a range having as endpoints any minimum frequency listed above and any maximum frequency listed above that is more frequent than the minimum frequency.

The duration of administration of an antigenic EGFRvIII peptide according to the invention, e.g., the period of time over which an antigenic EGFRvIII peptide is administered, can vary, depending on any of a variety of factors, e.g., patient response, etc. For example, an antigenic EGFRvIII peptide can be administered over a period of time ranging from about one day to about one week, from about two weeks to about four weeks, from about one month to about two months, from about two months to about four months, from about four months to about six months, from about six months to about eight months, from about eight months to about one year, from about one year to about two years, or from about two years to about four years, or more. In some embodiments, the EGFRvIII-targeting Qβ VLP may be administered as a once off treatment. In other embodiments, the EGFRvIII-targeting Qβ VLP may be administered for the life of the subject. In certain embodiments, the EGFRvIII-targeting Qβ VLP may be administered may be administered monthly (or every four weeks) until effective.

In some cases, the EGFRvIII-targeting Qβ VLP may be administered at an initial frequency for an initial period and then administered at a lower frequency thereafter. For example, a dosing regimen may include administering three doses of the EGFRvIII-targeting Qβ VLP at a frequency of once per month (i.e., an initial dose followed by a second dose one month after the initial dose and a third dose two month after the initial dose) followed by additional doses every three or four months after the initial two months.

When an EGFRvIII-targeting Qβ VLP composition is used for prophylactic treatment, it may be generally administered for priming and/or boosting doses. Boosting doses, when administered, are adequately spaced (e.g., yearly) to boost the level of circulating antibody that has fallen below a desired level. Boosting doses may include an EGFRvIII-targeting peptide either with or in the absence of the original immunogenic carrier. A booster composition may include an alternative immunogenic carrier or may be in the absence of any carrier. For example, a booster dose need not include the EGFRvIII-targeting VLP, but may include, for example, CDX-110. Moreover, a booster composition may be formulated either with or without adjuvant.

In some cases, the method can further include administering to the subject an additional therapeutic agent effective for treating the condition. For example, therapy involving the EGFRvIII-targeting Qβ VLP may be combined with conventional therapies for the cancer being treated. Conventional therapies can include radiation, surgical resection, chemotherapy, and/or immunotherapy.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

The amine-reactive arm of SMPH (Thermo Fisher Scientific, Waltham, Mass.) was linked to surface-exposed lysines on Qβ VLPs by reacting the VLPs with SMPH at a 1:10 molar ratio. Qβ-SMPH conjugates were purified by centrifugation using an Amicon Ultra-4 centrifugal filtration device. Qβ-SMPH was linked to the LEEK peptide by virtue the exposed sulfhydryl residue on the C-terminal cysteine residue of the peptide. Qβ-SMPH was reacted with the LEEK peptide at a 1:10 molar ratio and Qβ-LEEK conjugated particles (referred to as Qβ-EGFRvIII VLPs) were purified by centrifugation using the Amicon unit as described above. The extent of modification of VLPs was assessed by polyacrylamide gel electrophoresis.

Example 2

Groups of 10 mice were immunized with 5 μg of Qβ-EGFRvIII VLPs, 15 μg of CDX-110, 25 μg of CDX-110, or, as a control, 5 μg of wild-type Qβ VLPs. Sera were taken one, two, and three weeks after immunization, and IgG antibody responses were measured using a peptide-based ELISA. Briefly, Immulon II plates (Thermo Fisher Scientific, Waltham, Mass.) were coated with 100 μL of LEEK peptide (at 3 μg/mL) per well. After incubating overnight, wells were washed with PBS and then blocked using 5% Bovine Serum Albumin (BSA) in PBS, at 200 μL/well. Plates were incubated statically for two hours at 37° C., washed extensively with PBS, and then two-fold serial dilutions of mouse sera (diluted in 1% BSA/PBS, in a total volume of 100 μL) were added to the plate. Following incubation for two to three hours at room temperature, wells were extensively washed with PBS and then 100 μL of a 1:5000 dilution (in 1% BSA/PBS) of horseradish peroxidase-labeled goat anti-mouse IgG (Jackson ImmunoResearch, Inc., West Grove, Pa.) was added per well. After incubation for one hour at 37° C., wells were extensively washed with PBS and then 100 μL of TMB substrate (EMD Millipore) was added to each well. Plates were allowed to develop for 10-15 minutes at room temperature, and then 100 μL of stop solution (1% HCl) was added to each well. Plates were read using a microplate reader at an optical density of 450 nm (OD450). Wells were considered positive if the OD450 value was greater than the OD450 value of the negative control (a 1:100 dilution of pooled normal mouse serum).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

LEEKKGNYVVTDH  SEQ ID NO: 1

LEEKKGNYVVTDHC  SEQ ID NO: 2

What is claimed is:

1. An immunogen comprising:
   an immunogenic carrier comprising a Qβ bacteriophage virus-like particle (VLP); and
   an antigenic EGFRvIII peptide comprising LEEKKGNYVVTDH (SEQ ID NO:1) linked to the immunogenic carrier.

2. The immunogen of claim 1, wherein the immunogenic carrier is linked to the EGFRvIII peptide through a succinimidyl-6-[β-maleimidopropionamido]hexanoate (SMPH) cross-linker molecule.

3. A composition comprising the immunogen of claim 1.

4. An immunogenic composition comprising the immunogen of claim 1 and at least one adjuvant.

5. A method of treating cancer in an individual, the method comprising administering a therapeutically effective amount of an immunogen to the individual, the immunogen comprising:
   an immunogenic carrier comprising a Qβ bacteriophage virus-like particle (VLP); and
   an antigenic EGFRvIII peptide comprising LEEKKGNYVVTDH (SEQ ID NO:1) linked to the immunogenic carrier.

6. The method of claim 5, wherein the method further comprises administering to the individual at least one additional therapeutic agent for treating the cancer.

7. A nucleic acid encoding the immunogen of claim 1.

8. An expression vector comprising the nucleic acid of claim 7.

9. A host cell comprising the expression vector of claim 8.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

Leu Glu Glu Lys Lys Gly Asn Tyr Val Val Thr Asp His
1               5                   10

<210> SEQ ID NO 2
<211> LENGTH: 14
```

```
<212> TYPE: PRT
<213> ORGANISM: Artificial
<220> FEATURE:
<223> OTHER INFORMATION: Polypeptide

<400> SEQUENCE: 2

Leu Glu Glu Lys Lys Gly Asn Tyr Val Val Thr Asp His Cys
1               5                   10
```